United States Patent
Khoo et al.

(10) Patent No.: US 8,153,691 B2
(45) Date of Patent: Apr. 10, 2012

(54) METHOD FOR PREPARING COMPOSITIONS FOR PREVENTING OR TREATING INFLAMMATORY BOWEL DISEASE

(75) Inventors: Christina Khoo, Lawrence, KS (US); William David Schoenherr, Hoyt, KS (US); Kathy Lynn Gross, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 12/474,493

(22) Filed: May 29, 2009

(65) Prior Publication Data

US 2009/0253791 A1 Oct. 8, 2009

Related U.S. Application Data

(62) Division of application No. 11/617,810, filed on Dec. 29, 2006, now Pat. No. 8,048,922.

(51) Int. Cl.
*A61K 31/202* (2006.01)
(52) U.S. Cl. ........................................... 514/560
(58) Field of Classification Search .................. None
See application file for complete search history.

(56) References Cited

FOREIGN PATENT DOCUMENTS

| WO | 0182720 | A1 | 11/2001 |
|---|---|---|---|
| WO | 2004075653 | A1 | 9/2004 |
| WO | 2004/112776 | * | 12/2004 |
| WO | 2004112776 | A2 | 12/2004 |
| WO | 2006072084 | A2 | 7/2006 |

OTHER PUBLICATIONS

Html version of the file http://www.hillsvet.com/media/_refacing/USARG/generalContent/vet/confProceedings/en/pdf/felineCare_EvidenceBasedUseFattyAcidsFelineDisease_en.pdf, retrieved from the web Feb. 8, 2011.*
2005 AAFCO Official Publication, pp. 137-140.
Small Animal Nutrition, pp. 127-146 (2000).

* cited by examiner

*Primary Examiner* — Phyllis G. Spivack
(74) *Attorney, Agent, or Firm* — Shannon McGarrah

(57) ABSTRACT

A method for preparing compositions, comprising docosahexaenoic acid (DHA) and optionally one or more fatty acids selected from the group consisting of eicosapentaenoic acid (EPA), arachidonic acid (ARA), linoleic acid (LA), and α-linoleic acid (ALA), that are administered to felines for treating feline inflammatory bowel disease (IBD).

5 Claims, No Drawings

METHOD FOR PREPARING COMPOSITIONS FOR PREVENTING OR TREATING INFLAMMATORY BOWEL DISEASE

CROSS-REFERENCE TO PRIOR APPLICATIONS

This application is a divisional of U.S. patent application Ser. No. 11/617,810 filed Dec. 29, 2006, which claims priority from U.S. Provisional Application No. 60/754,806 filed on Dec. 29. 2005. the contents of which are incorporated herein by reference in their entirety for all purposes.

BACKGROUND OF THE INVENTION

1. Field of the Invention

The invention relates generally to compositions and methods for presenting or treating inflammatory bowel disease and particularly to the use of docosahexaenoic acid for preventing or treating feline inflammatory bowel disease.

2. Description of the Related Art

The terms "inflammatory bowel disease" or "IBD" refer to a group of chronic idiopathic gastrointestinal disorders characterized by inflammatory infiltrates within the lamina propria of the gastrointestinal tract. IBD encompasses segmental granulomatous enterocolitis, lymphoplasmacytic enteritis, eosinophilic gastroenterocolitis, lymphocytic gastroenterocolitis, suppurative enterocolitis, and histiocytic colitis. The lymphoplasmacytic form is probably the most common type of IBD. These specific types of IBD are characterized based on the type of inflammatory infiltrate found in the lamina propria. The inflammatory infiltrates can be quite variable in terms of severity and cell types, with lymphocytes and plasma cells being the most common cell types. Inflammatory infiltrates may involve the stomach, small bowel, and colon. In cats, for example, the stomach and small bowel are affected most often. In many cases, multiple segments of the bowel are involved and clinical signs may be mixed, reflecting the broad distribution of mucosal lesions. The severity of IBD varies from mild clinical signs to life-threatening protein-losing enteropathies.

Mucosal inflammatory infiltrates are responsible for the clinical manifestations of IBD. Mucosal inflammation disrupts normal absorptive processes. Such disruption results in malabsorption and osmotic diarrhea. Altered gut permeability can result in leakage of fluid, protein, and blood into the gut lumen. Malabsorbed fats, carbohydrates, and bile acids result in secretory diarrhea. Inflammatory mediators may also directly trigger intestinal secretion and mucus production by goblet cells. Mucosal inflammatory infiltrates may alter intestinal and colonic motility patters, a mechanism attributed to the influence of prostaglandins and leukotrienes on smooth muscle. Inflammation of the stomach and small bowel stimulates receptors that trigger vomiting. In cats, for example, the most common clinical signs of IBD are chronic vomiting, diarrhea, and weight loss.

The fundamental pathway for the development of IBD involves hypersensitivity. Two related theories attempt to explain the underlying cause for hypersensitivity reactions. The first theory speculates that felines with IBD develop a defect in the intestinal mucosal barrier. Loss of mucosal integrity results in increased gut permeability and hypersensitivity responses to allergens that are normally tolerated. The second theory speculates that IBD results from aberrant immunological responses to luminal antigens. Both potential pathways culminate in release of inflammatory mediators. These substances may further damage the intestinal mucosal surface and set up a cycle of inflammation and loss of barrier function.

Essential fatty acids have specific roles in cell function regulation. For example, the omega-3 eicosapentaenoic acid (EPA), and the omega-6 arachidonic and gamma-linolenic acids are precursors for the synthesis of eicosanoids which are immunoregulatory molecules functioning as local hormones and mediators of inflammation. The eicosanoids synthesized from arachidonic acid (ARA) are proinflammatory compared to eicosanoids produced from eicosapentaenoic and gamma-linolenic acids, and may result in pathologic conditions when produced in excessive amounts. Macrophages are a significant source of eicosanoids, and modulate the intensity and duration of inflammatory and immune responses. The predominant polyunsaturated fatty acid in membrane phospholipids of macrophages and lymphocytes is ARA. Administration of gamma-linolenic or EPA results in the replacement of ARA in the macrophage membrane with eicosapentaenoic or gamma-linolenic acid. The result of such replacement is the production of fewer ARA-derived eicosanoids and more EPA-derived or gamma-linolenic acid-derived eicosanoids, thereby reducing the immunologic response to an inflammatory episode.

A definitive diagnosis of IBD is based on the histopathological examination of mucosal or full-thickness intestinal biopsy specimens collected by endoscopic or surgical techniques. Thus, there is a need for alternative methods for diagnosing feline IBD that are less invasive than obtaining biopsy specimens. There is also a need for new methods and compositions useful for preventing and treating feline IBD.

SUMMARY OF THE INVENTION

It is, therefore, an object of the invention to provide methods for preventing or treating IBD in felines.

It is another object of the invention to provide compositions suitable for preventing or treating IBD in felines.

It is another object of the invention to provide methods for determining if a feline is suffering from IBD.

It is a further object of the invention to provide articles of manufacture in the form of kits that contain combinations of foods, compounds, ingredients, and devices useful for preventing or treating IBD in felines.

It is another object of the invention to provide means for communicating information about the methods, compositions, articles of manufacture, and benefits of the invention.

One or more of these and other objects are achieved using novel methods for preventing and/or treating IBD in felines susceptible to or suffering from IBD comprising administering to the felines a therapeutically-effective amount of docosahexaenoic acid (DHA). Methods for diagnosing IBD and kits comprising combinations of foods, compounds, ingredients, and devices useful for preventing and/or treating IBD are also provided.

Additional objects, features, and advantages of the invention will be apparent to those skilled in the art.

DETAILED DESCRIPTION OF THE INVENTION

In one aspect, the invention provides methods for treating IBD in a feline suffering from IBD. Treating IBD includes ameliorating, suppressing, and/or eradicating IBD. Those skilled in the art can diagnose IBD (and distinguish IBD from other gastrointestinal diseases) utilizing diagnostic tests (e.g., complete blood cell count, serum biochemistry, serum thyroxine level, immunodeficiency virus test, feline leukemia virus test, urinalysis, fecal examinations for parasites and bacteria); dietary trials; abdominal radiographs and/or ultrasound; and/or examination of mucosal or full-thickness intestinal biopsy specimens. In another aspect, the invention provides methods for preventing IBD in a feline susceptible to developing IBD. Preventing IBD includes reducing the risk of IBD, delaying the onset of IBD, and/or keeping a feline from developing IBD. The methods comprise administering to the feline a therapeutically-effective amount of docosahexaenoic acid (DHA). A therapeutically-effective amount is an amount that will achieve the goal of treating IBD when the feline is suffering from IBD, or preventing IBD when the feline is susceptible to developing IBD, or lowering the level of CD4+ lymphocytes and neutrophils in a feline susceptible to or suffering from IBD. Administering means introducing DHA or other compounds into the feline in a suitable dosage form by a suitable administration route (e.g., orally, topically, or parenterally). DHA can be administered, for example, as pure DHA or DHA derivative (e.g., a salt such as an ester) or as a composition comprising DHA and/or DHA derivative(s). References herein to DHA and other fatty acids herein include the derivatives of such compounds. A DHA-comprising composition may also comprise one or more conventional pharmaceutically-acceptable excipients (e.g., adjuvants, carriers, and/or vehicles). In some embodiments, the DHA-comprising composition may comprise a food composition.

The invention is based upon the surprising discovery that DHA, but not EPA or other similar fatty acids, is useful for preventing or treating IBD in felines and that DHA may have the opposite effect in other animals. While EPA and related fatty acids alone or in combination do not prevent or treat IBD, they are useful for supplementing DHA in preventing or treating IBD. Thus, the unexpected result that DHA alone or DHA in combination with EPA and related fatty acids is effective for preventing or treating IBD when administered to felines in a therapeutically-effective amount.

DHA effectively lowers the level of CD4+ lymphocytes and neutrophils in a feline, including a feline susceptible to or suffering from IBD, when DHA is administered in a therapeutically-effective amount, as described herein.

In some embodiments, the methods comprise administering to the feline from about 6 to about 165 mg/kg body weight/day DHA. In some such embodiments, from about 12 to about 65 mg/kg body weight/day DHA is administered to the feline. In others, from about 12 to about 32 mg/kg body weight/day DHA is administered to the feline. The daily amount of DHA can be administering in a single dose or, alternatively, in two or more dosages that make up the daily dose.

In some embodiments, administering DHA comprises feeding DHA to the feline, i.e., feeding DHA or a composition comprising DHA (including DHA derivatives).

In various embodiments, a DHA-comprising composition fed to the feline comprises a food composition. In some embodiments, the food composition meets the AAFCO's minimum nutrient level requirements for reproduction or maintenance. See 2005 AAFCO Official Publication, pages 137-40. In some embodiments, the food composition comprises a dry food. In others, the food composition comprises a semi-moist food. In still others, the food composition comprises a moist food. The terms, "dry", "moist" and "semi-moist", as used herein, are familiar to one of skill in the art. The food composition may be a supplement, treat, snack, or partially or fully edible toy. In some embodiments, the composition comprises a mixture of one or more foods or a hypoallergenic food composition.

In some embodiments, the feline is a companion feline. A companion feline can be a feline kept as a pet. A companion feline can also be a feline from a widely domesticated species, for example, cats (*Felis domesticus*) regardless of whether or not it is kept as a pet. In some embodiments, the feline is a growing feline. A growing feline is one that has not reached adult size. For example, a growing cat typically is one that is less than about one year old. In some embodiments, the feline is an adult feline. An adult feline is a feline of any age after juvenile growth and development has been completed, including senior and geriatric felines. For example, an adult cat typically is one that is from about one year old through the remainder of its life. A senior feline is one of an age at which it is at a risk for suffering from an age-related disease regardless of whether or not the feline shows obvious physical or behavioral signs of aging. For example, a senior cat typically is a cat from about seven to about eleven years old. A geriatric feline is a feline showing signs of advanced age. For example, a geriatric cat typically is a cat of about twelve years of age and beyond.

Unless otherwise stated, all percentages herein are weight percentages on a dry matter basis. The term "dry matter basis" means that an ingredient's concentration in a composition is measured after any moisture in the composition is removed.

In some embodiments, the composition administered to the feline comprises from about 0.05 to about 1% DHA. In some such embodiments, the composition comprises from about 0.1 to about 0.4% DHA. In others, the composition comprises from about 0.1 to about 0.2% DHA. In yet other such embodiments, the composition comprises from about 0.05 to about 0.2% DHA. In further such embodiments, the composition comprises from about 0.05 to about 0.15% DHA. And in yet further such embodiments, the composition comprises from about 0.05 or about 0.1 to about 0.15, about 0.2, or about 0.4% DHA.

In additional embodiments, the composition administered to the feline further comprises at least one fatty acid selected from the group consisting of eicosapentaenoic acid (EPA), arachidonic acid (ARA), linoleic acid (LA), and α-linoleic acid (ALA). In some such embodiments, the composition comprises from about 0.05 to about 1% of each fatty acid present in the composition. In other such embodiments, the composition comprises from about 0.1 to about 0.5% or from 0.1 to about 0.3% of the fatty acid. In one embodiment, the composition administered to the feline further comprises from about 0.05 to about 1% EPA. In some such embodiments, the composition comprises from about 0.1 to about 0.5% EPA. In other such embodiments, the composition comprises from about 0.1 to about 0.3% EPA. In yet other such embodiments, the composition comprises from about 0.05 to about 0.3% EPA. In further such embodiments, the composition comprises from about 0.15 to about 0.3% EPA. In yet further such embodiments, the composition comprises from about 0.05, about 0.1, or about 0.15 to about 0.2, about 0.3, about 0.4, or about 0.5% EPA.

In some embodiments, the composition administered to the feline comprises from about 0.05 to about 1% DHA and from about 0.05 to about 1% EPA, and the ratio of the amount of EPA present in the composition to the amount of DHA in the composition is from about 1 to about 2. In some such embodiments, the ratio of the amount of EPA present in the composition to the amount of DHA present in the composition is from about 1.2 to about 1.8. In other such embodiments, the ratio of the amount of EPA in the composition to the amount of DHA in the composition is from about 1.2 to about 1.5. In yet other such embodiments, the ratio of the amount of EPA present in the composition to the amount of DHA present in the composition is from about 1.3 to about 1.6. And in further such embodiments, the ratio of the amount of EPA present in the composition to the amount of DHA present in the composition is from about 1, about, 1.2, or about 1.3 to about 1.5, about 1.6, about 1.8, or about 2.

In some embodiments, the methods of prevention and treatment further comprise administering to the feline an anti-inflammatory bowel disease (anti-IBD) agent in conjunction with administering DHA or the combination of DHA and at least one fatty acid selected from the group consisting of EPA, ARA, LA, and ALA. An anti-IBD agent is a compound, a derivative thereof (e.g., a salt, solvate, or hydrate of the compound), or a composition comprising such compounds and/or derivatives that is used to prevent or treat IBD. "In conjunction" means that an anti-IBD agent is administered to the feline either together with DHA or separately from DHA at the same or different frequency via the same or different administration route and either at about the same time as DHA or periodically. "At about at the same time" generally means that the anti-IBD agent is either administered when DHA is administered to the feline or within about 72 hours after administering DHA to the feline. "Periodically" generally means that an anti-IBD agent is administered to a feline following a dosage schedule suitable for administering the agent while a DHA-comprising composition is fed to the feline routinely as appropriate for that feline. Thus, the term "in conjunction" specifically includes situations when an anti-IBD agent is administered to a feline for a prescribed period of time while DHA is administered to the feline for a much longer period of time (e.g., for life). If more than one agent is administered to a feline, the dosage form and route of administration for each agent may vary. Those skilled in the art would understand that one or more anti-IBD agents can be administered to a feline while the feline is fed a single DHA-comprising composition or, alternatively, when the feline is fed different DHA-comprising compositions for varying time intervals.

Suitable anti-IBD agents include, for example, corticosteroids (e.g., prednisone, prednisolone), immunosuppresants (e.g., azathiprine), and antibiotics (e.g., metronidazole, amoxicillin, tylosin). Anti-IBD agents can be administered, for example, in the form of salts derived from inorganic or organic acids. Depending on the particular compound, a salt of the compound may be advantageous due to one or more of the salt's physical properties, for example, enhanced pharmaceutical stability in differing temperatures and humidity, or a desirable solubility in water or oil. The salt preferably is a pharmaceutically-acceptable salt.

The preferred total daily dose of an anti-IBD agent (administered in either single or divided doses) is typically from about 0.001 to about 100 mg/kg body weight, more preferably from about 0.01 to about 30 mg/kg body weight, and even more preferably from about 0.01 to about 10 mg/kg body weight. Dosage unit compositions can contain such amounts and submultiples thereof to make up the daily dose. In many instances, the administration of the anti-IBD agent will be repeated a plurality of times. Multiple doses per day typically may be used to increase the total daily dose, if desired. Factors affecting the preferred dosage regimen include, for example, the age, weight, and condition of the feline; the severity of the disease; the route of administration; pharmacological considerations, such as the activity, efficacy, pharmacokinetic, and toxicology profiles of the particular anti-IBD agent used; whether a drug delivery system is utilized; and whether the anti-IBD agent is administered as part of a drug combination. Thus, the dosage regimen can vary widely, and therefore, can differ from the preferred dosage regimen discussed above.

In yet another aspect, the invention provides compositions suitable for preventing and/or treating IBD in a feline. These compositions are described and exemplified in the context of the methods herein for preventing and/or treating IBD in a feline.

In a further aspect, the invention provides methods for preparing the compositions suitable for use in methods of prevention and treatment of IBD. Such compositions can be prepared, for example, by mixing two or more ingredients (including food compositions) that, when combined, yield a composition of the invention or by mixing one or more food compositions with additional ingredient(s) such as, for example, DHA, EPA, and/or an anti-IBD agent. Such compositions can also be prepared by one or more of the methods discussed in, for example, Small Animal Nutrition, pages 127-46 (2000).

In yet further aspect, the invention provides for a use of DHA and optionally at least one fatty acid selected from the group consisting of EPA, ARA, LA, and ALA to prepare a composition of the invention suitable for preventing or treating feline IBD. In some embodiments, the invention provides a use of DHA to prepare a composition comprising from about 0.05 to about 1% DHA. In some such embodiments, the composition comprises from about 0.1 to about 0.4% DHA. In others, the composition comprises from about 0.1 to about 0.2% DHA. In yet other such embodiments, the composition comprises from about 0.05 to about 0.2% DHA. In further such embodiments, the composition comprises from about 0.05 to about 0.15% DHA. In yet further such embodiments, the composition comprises from about 0.05 or about 0.1 to about 0.15, about 0.2, or about 0.4% DHA. In some embodiments, the composition comprises a food composition.

In some embodiments, the invention provides a use of DHA and at least one fatty acid selected from the group consisting of EPA, ARA, LA, and ALA, preferably EPA, to prepare a composition comprising from about 0.05 to about 1% DHA and from about 0.05 to about 1% of each of EPA, ARA, LA, and/or ALA present in the composition to prevent and/or treat feline IBD. In some such embodiments, the composition comprises from about 0.1 to about 0.4% DHA and from about 0.1 to about 0.5% of one or more of EPA, ARA, LA, and/or ALA. In other such embodiments, the composition comprises from about 0.1 to about 0.2% DHA and from about 0.1 to about 0.3% of one or more of EPA, ARA, LA, and/or ALA. In yet other such embodiments, the composition comprises from about 0.05 to about 0.2% DHA and from about 0.05 to about 0.3% of one or more of EPA, ARA, LA, and/or ALA. In further such embodiments, the composition comprises from about 0.05 to about 0.15% DHA and from about 0.15 to about 0.3% of one or more of the fatty acids. In yet further such embodiments, the composition comprises from about 0.05 or about 0.1 to about 0.15, about 0.2, or about 0.4% DHA and from about 0.05, about 0.1, or about 0.15 to about 0.2, about 0.3, about 0.4, or about 0.5% of one or more of the fatty acids. In some embodiments, the composition comprises a food composition.

In some embodiments, the invention provides a use of DHA and EPA to prepare a composition comprising from about 0.05 to about 1% DHA and from about 0.05 to about 1% EPA wherein the ratio of the amount of EPA present in the composition to the amount of DHA present in the composition is from about 1 to about 2 to prevent and/or treat feline IBD. In some such embodiments, the ratio of the amount of EPA in the composition to the amount of DHA present in the composition is from about 1.2 to about 1.8. In other such embodiments, the ratio of the amount of EPA present in the composition to the amount of DHA present in the composition is from about 1.2 to about 1.5. In other such embodiments, the ratio of the amount of EPA present in the composition to the amount of DHA present in the composition is from about 1.3 to about 1.6. In further such embodiments, the ratio of the amount of EPA present in the composition to the amount of DHA in the composition is from about 1, about, 1.2, or about 1.3 to about 1.5, about 1.6, about 1.8, or about 2. In some embodiments, the composition comprises a food composition.

In a further aspect, the invention provides a method for determining if a feline is suffering from IBD. The method comprises dividing lymphocytes collected from blood obtained from the feline into a first, second, and third sample comprising equal amounts of lymphocytes; exposing the second sample to an amount of a mitogen for a period of time; exposing the third sample to the same amount of the same mitogen as the second sample for the same period of time as the second sample in the presence of an amount of DHA; and comparing the levels of lymphocyte proliferation in all samples. The feline has IBD if the level of lymphocyte proliferation in the second sample is higher than the level of lymphocyte proliferation in the first sample, and the level of lymphocyte proliferation in the third sample is lower than the level of lymphocyte proliferation in the second sample.

Lymphocytes are collected from blood obtained from a feline and are divided into samples comprising equal amounts of lymphocytes. Procedures for obtaining blood from felines, isolating the lymphocytes from that blood, and counting the lymphocytes are known to those skilled in the art. In some embodiments, lymphocytes can be collected as described in Example 1. The lymphocytes isolated from a feline's blood are divided into three or more samples with all samples comprising equal amounts of lymphocytes. In some embodiments, the lymphocytes are divided into three samples (i.e., a first, second, and third sample). One of those samples (i.e., the first sample) is used as a control. One of the remaining two samples (i.e., the second sample) is exposed to an amount of mitogen for a period of time, and the other (i.e., the third sample) is exposed to the same amount of mitogen as the second sample for the same period of time as the second sample in the presence of an amount of DHA. All samples are incubated for the same period of time at the same temperature.

A mitogen is an agent that triggers mitosis. Any mitogen that can trigger mitosis of feline lymphocytes is suitable for the method of the invention. In some embodiments, the mitogen is a polyclonal mitogen. A polyclonal mitogen is a mitogen that induces mitosis in lymphocytes of many different specificities or clonal origins. Mitogens suitable for the method of IBD diagnosis of the invention include, for example, phytohemagglutinin (PHA), concanavalin (ConA), pokeweed mitogen (PWM), lipopolysaccharide (LPS), and anti-CD3 antibody.

Procedures for measuring lymphocyte proliferation are known to those skilled in the art. Any procedure for measuring in vitro lymphocyte proliferation is suitable for the method of the invention. In vitro lymphocyte proliferation can be measured directly (e.g., by counting cells or by determining the mitotic index) or indirectly (e.g., by determining the rate of overall metabolic activity in a lymphocyte population or by monitoring the synthesis of deoxyribonucleic acid (DNA)). In some embodiments, in vitro lymphocyte proliferation is measured as discussed in Example 1.

In some embodiments of the method of the invention, lymphocyte proliferation is measured by monitoring DNA synthesis. Procedures for monitoring and measuring DNA synthesis are known to those skilled in the art. Any procedure for monitoring and measuring DNA synthesis is suitable for the method of the invention. DNA synthesis can be monitored and measured by, for example, labeling the DNA of mitotically active cells with $^3$H-thymidine or 5-bromo-2'-deoxyuridine (BrdU) and then determining the amount of $^3$H-thymidine or BrdU that was incorporated into DNA. In some embodiments, DNA synthesis is measured as discussed in Example 1.

As discussed above, a determination if a feline is suffering from IBD is made by comparing the levels of in vitro lymphocyte proliferation in the first, second and third samples. If the level of lymphocyte proliferation in the second sample (i.e., the sample treated with a mitogen, but no DHA) is higher than the level of lymphocyte proliferation in the first sample (i.e., the control sample that was not treated with mitogen or DHA), then the mitogen used in the assay has indeed stimulated in vitro lymphocyte proliferation in the second and third sample. If that is the case, then the level of lymphocyte proliferation in the third sample (i.e., the sample treated with both the mitogen and DHA) is compared to the level of lymphocyte proliferation in the second sample. If the level of lymphocyte proliferation in the third sample is lower than the level of lymphocyte proliferation in the second sample, then DHA had inhibited the pro-inflammatory effect of the mitogen indicating that the feline has IBD.

In a further aspect, the invention provides an article of manufacture in the form of a kit suitable for preventing or treating IBD. The kit comprises DHA or a DHA-comprising composition of the invention. In some embodiments, the kit further comprises an anti-IBD agent (i.e., the kit comprises one or more anti-IBD agents). In some embodiments, the kit further comprises instructions for one or more of (a) administering DHA to a feline, (b) administering an anti-IBD agent to a feline in conjunction with administering DHA to the feline, (c) preventing and/or treating IBD in a feline by administering DHA to the feline, and (d) preventing and/or treating IBD in a feline by administering an anti-IBD agent in conjunction with administering DHA to the feline.

In some embodiments, the kit comprises a DHA-comprising food composition. In some embodiments, the kit further comprises an anti-IBD agent. In some embodiments, the kit further comprises instructions for one or more of (a) feeding the DHA-comprising food composition to a feline, (b) administering an anti-IBD agent to a feline in conjunction with feeding the DHA-comprising food composition to the feline, (c) preventing and/or treating IBD in a feline by feeding the feline a DHA-comprising food composition, and (d) preventing and/or treating IBD in a feline by administering to the feline an anti-IBD agent in conjunction with feeding the feline a DHA-comprising food composition.

In a further aspect, the invention provides an article of manufacture in the form of a kit comprising two or more ingredients that, when combined together and, optionally, with additional ingredients that are or are not a part of the kit, yield a DHA-comprising composition of the invention suitable for preventing and/or treating IBD in a feline. One of the two or more ingredients that are to be combined can be, for example, pure DHA or derivative thereof or a composition comprising DHA. Another one of the two or more ingredients that are to be combined can be, for example, a food composition. If, to prepare a composition, additional ingredients that are or are not a part of the kit are needed, the kit provides instructions about those ingredients. In some embodiments, the kit further comprises an anti-IBD agent. In some embodiments, the kit further comprises instructions for one or more of (a) preparing the composition by combining the two or more ingredients and, optionally, additional ingredients that are or are not a part of the kit, (b) feeding the composition to a feline to, for example, prevent and/or treat IBD, (c) administering an anti-IBD agent to the feline in conjunction with feeding the feline the composition, (d) preventing and/or treating IBD in a feline by feeding the feline the composition, and (e) preventing and/or treating IBD in a feline by administering to the feline an anti-IBD agent in conjunction with feeding the feline the composition.

In some embodiments, the kit comprises in separate containers in a single package or in separate containers in a virtual package, as appropriate for the kit component, either (A) DHA, (B) a composition comprising DHA, or (C) two or more ingredients that, when combined together, and, optionally, with additional ingredients that are or are not a part of the kit, yield a composition comprising DHA, and one or more of (1) at least one fatty acid selected from the group consisting of EPA, ARA, LA, and ALA, (2) a food composition suitable for consumption by a feline susceptible to or suffering from inflammatory bowel disease, (3) an anti-IBD agent, and (4) instructions for one or more of (a) preparing a composition comprising DHA alone or in combination with at least one fatty acid selected from the group consisting of EPA, ARA, LA, and ALA, (b)) preparing a food composition suitable consumption by a feline susceptible to or suffering from inflammatory bowel disease comprising a therapeutically-effective amount of DHA alone or in combination with at least one fatty acid selected from the group consisting of EPA, ARA, LA, and ALA, (c) administering DHA alone or in combination with at least one fatty acid selected from the group consisting of EPA, ARA, LA, and ALA to a feline to prevent and/or treat IBD, (d) preventing and/or treating IBD in a feline by feeding the feline a composition comprising DHA alone or in combination with at least one fatty acid selected from the group consisting of EPA, ARA, LA, and ALA, (e) administering an anti-IBD agent to a feline in conjunction with feeding the feline a composition comprising DHA alone or in combination with at least one fatty acid selected from the group consisting of EPA, ARA, LA, and ALA, and (f) preventing and/or treating IBD in a feline by administering to the feline an anti-IBD agent in conjunction with feeding the feline a composition comprising DHA alone or in combination with at least one fatty acid selected from the group consisting of EPA, ARA, LA, and ALA.

The term "single package" generally means that the components of a kit are physically associated in or with one or more containers and considered as a unit of manufacture, distribution, sale, or use. Containers include, for example, bags, boxes, bottles, shrink wrap packages, stapled or otherwise fixed components, and combinations thereof. A single package can be, for example, containers or individual food compositions physically associated such that they are considered a unit for manufacture, distribution, sale, or use. The term "virtual package" generally means that the components of a kit are associated by directions on one or more physical or virtual kit components instructing the user how to obtain additional components, e.g., in a bag containing one component and directions instructing the user to go to a website, contact a recorded message, view a visual message, or contact a caregiver to obtain instructions on how to use the kit. When the kit comprises a virtual package, the kit is limited to instructions in a virtual environment with one or more physical kit components.

In a further aspect, the invention provides a means for communicating information about or instructions for one or more of (1) using DHA or a composition comprising DHA to prevent and/or treat IBD in a feline, (2) preventing and/or treating IBD in a feline by administering to the feline an anti-IBD agent in conjunction with feeding the feline DHA or a composition comprising DHA, and (3) using a kit of the invention for preventing and/or treating IBD in a feline comprising a document, digital storage media, optical storage media, audio presentation, or visual display containing the information or instructions. In some embodiments, the communicating means comprises a document, digital storage media, optical storage media, audio presentation, or visual display containing the information or instructions. Preferably, the communication means is a displayed web site or a brochure, product label, package insert, advertisement, or visual display containing such information or instructions. Useful information or instructions include, for example, (1) information and instructions how to use a composition, method, or kit of the invention and (2) contact information for animal caregivers if they have a question about the invention and its uses.

In a further aspect, the present invention provides for a use of DHA and optionally at least one fatty acid selected from the group consisting of EPA, ARA, LA, and ALA to prepare a medicament. In another, the invention provides for the use of a therapeutically-effective amount of such fatty acid(s) to prepare a medicament for preventing or treating feline IBD. Generally, medicaments are prepared by admixing a compound or composition with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise. Similarly, the words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications and publications mentioned herein are incorporated herein by reference to the extent allowed by law for the purpose of describing and disclosing the compounds, processes, techniques, procedures, technology, articles, and other compositions and methods disclosed therein that might be used with the present invention. However, nothing herein is to be construed as an admission that the invention is not entitled to antedate such disclosure by virtue of prior invention.

EXAMPLES

The invention can be further illustrated by the following examples, although it will be understood that the examples are included merely for purposes of illustration and are not intended to limit the scope of the invention unless otherwise specifically indicated.

Example 1

This example illustrates the effect of DHA and EPA on in vitro lymphocyte proliferation of lymphocytes obtained from the blood of healthy cats and cats with IBD.

The study utilizes eleven healthy cats and eleven cats with IBD. The cats with IBD are diagnosed by an intestinal biopsy, and have a history of chronic diarrhea. For six weeks, all cats are fed a nutritionally adequate dry food indicated for gastrointestinal distress. Blood is drawn from all cats at four, five, and six weeks. Samples with equal amounts of lymphocytes are used in an in vitro lymphocyte proliferation assay.

More specifically, 4.5 ml blood is mixed with 4.5 ml HBSS (Hank's Balanced Salt Solution) +25 mM HEPES. 4 ml of Ficoll-Paque Plus (Amersham) are slowly injected under the diluted blood. The mixture is centrifuged for twenty minutes at 500 g at 25° C. The upper layer is discarded. The lymphocytes are transferred into a clean tube, resuspended in 6 ml of HBSS+25 mM HEPES, and then centrifuged for ten minutes at 200 g at 25° C. The supernatant is discarded, and the lymphocytes are washed with 6 ml of HBSS. This centrifugation and wash step is repeated two more times. The washed lymphocytes are then resuspended in 5 ml of AIM medium (Invitrogen). Samples with 200,000 lymphocytes in 100 μl of AIM medium are used for the lymphocyte proliferation assay.

The lymphocyte proliferation assay is performed utilizing Amersham's Biotrak cell proliferation ELISA system, version 2. Lymphocyte samples are incubated in a 96-well plate with 7 μg/ml PHA (phytohemagglutinin) in the absence or presence of 12.5 μM and 25 μM DHA or EPA in a 37° C. incubator with 5% $CO_2$ and 90% humidity for forty hours. After that, 20 μl of 100 μM BrdU is added, and the samples are incubated for two hours at 37° C. The plates are then removed from the incubator and centrifuged at 300 g for ten minutes at 25° C. The medium is removed by tapping and blotting, and the cells are dried in a chemical fume hood for at least fifteen minutes, 200 μl of fixative is added to every well and the plate is incubated for thirty minutes at room temperature. The cell fixative is removed by tapping and blotting, 200 μl of blocking buffer are added to every well, and the plate is incubated for thirty minutes at room temperature. The blocking buffer is removed by tapping and blotting, and 100 μl of anti-BrdU working solution is added to each well and incubated for ninety minutes at room temperature. The anti-BrdU solution is removed by tapping and blotting, and each well is rinsed three times with 300 μl washing solution. 100 μl 3,3',5,5'-tetramethylbenzidine is added to each well and incubated for ten minutes or until color intensity is achieved. 25 μl 1M sulfuric acid is added to stop the reaction, and the plate is read on a fusion microplate reader (PerkinElmer) within five minutes. The results from the in vitro proliferation assay are presented in tables 1 and 2.

TABLE 1

Effect of DHA on Lymphocyte Proliferation

|  | no PHA | PHA | PHA + 12.5 μM DHA | PHA + 25 μM DHA |
| --- | --- | --- | --- | --- |
| Healthy cats | 0.05 ± 0.05 | 0.32 ± 0.21 | 0.28 ± 0.19 | 0.25 ± 0.17 |
| Cats with IBD | 0.09 ± 0.11 | 0.58 ± 0.26 | 0.49 ± 0.15 | 0.45 ± 0.18 |

TABLE 2

Effect of EPA on Lymphocyte Proliferation

|  | no PHA | PHA | PHA + 12.5 μM EPA | PHA + 25 μM EPA |
| --- | --- | --- | --- | --- |
| Healthy cats | 0.05 ± 0.05 | 0.32 ± 0.21 | 0.38 ± 0.23 | 0.37 ± 0.23 |
| Cats with IBD | 0.09 ± 0.11 | 0.58 ± 0.26 | 0.62 ± 0.27 | 0.63 ± 0.29 |

As can be seen from Tables 1 and 2, the proliferation activity of the lymphocytes obtained from the blood of the cats with IBD is higher than the proliferation activity of the lymphocytes obtained from the blood of the healthy cats. Incubation of lymphocytes from the cats with IBD with both 12.5 and 25 μM DHA results in a decrease in lymphocyte proliferation. Incubation of lymphocytes from the cats with IBD with both 12.5 and 25 μM EPA does not result in a decrease in lymphocyte proliferation.

Example 2

This example illustrates the effect of DHA and EPA on the cytokine profile of lymphocytes obtained from the blood of healthy cats and cats with IBD.

Lymphocytes are obtained from the blood of healthy cats and cats with IBD as described in Example 1 and then treated with DHA or EPA also as described in Example 1. Ribonucleic acid (RNA) is extracted from all samples, and real time polymerase chain reaction (RT-PCR) is performed to examine the changes in the level of expression of the following cytokines: interleukins 1α, 1β, 2, 6, and 10 (IL-1α, IL-1β, IL-2, IL-6, and IL-10), macrophage inhibitory factor (MIF), interferon gamma (IFN-γ), and transforming growth factor beta (TGF-β). The results from the cytokine PCR analysis are presented in Table 3.

TABLE 3

Effect of DHA and EPA on Cytokine Expression

|  | IL-1α | IL-6 | MIF | IL-2 | IFN-γ | IL-1β | IL-10 | TGF-β |
|---|---|---|---|---|---|---|---|---|
| Healthy cats (no PHA) | 1 | 1 | 1 | 1 | 1 | 1 | 1 | 1 |
| Healthy cats (PHA) | 0.82 | 3.55 | 12.25 | 1.03 | 5.95 | 1.03 | 0.65 | 1.1 |
| Healthy cats (PHA + DHA) | 0.86 | 5.75 | 16.9 | 21.05 | 37.6 | 0.87 | 0.95 | 3.55 |
| Healthy cats (PHA + EPA) | 1.05 | 10.6 | 14.05 | 59.4 | 130.9 | 1.17 | 1.2 | 4.7 |
| Cats with IBD (no PHA) | 0.355 | * | 0.56 | 39.25 | 106 | 0.53 | 1.4 | 6.9 |
| Cats with IBD (PHA) | 0.57 | 5.1 | 10.45 | 7.9 | 23.75 | 0.63 | 0.37 | 6.95 |
| Cats with IBD (PHA + DHA) | 0.57 | 13.9 | 6.55 | 3 | 4.9 | 1.85 | 0.45 | 1.45 |
| Cats with IBD (PHA + EPA) | 0.46 | 6.45 | 4.45 | 1.89 | 4.45 | 1.34 | 0.34 | 2.4 |

* = undetected
DHA = 12.5 μM DHA
EPA = 12.5 μM EPA

Referring to Table 3, the level of expression of the proinflammatory interleukins IL-2 and IFN-γ is much higher in cats with IBD compared to healthy cats, indicating the presence of inflammation. The level of expression of the anti-inflammatory cytokine TGF-β is slightly higher in cats with IBD compared to healthy cats, probably to counteract inflammation. DHA decreases the level of expression of IL-2 and IFN-γ in cats with IBD to a level similar to the level of expression of IL-2 and IFN-γ in the healthy cats stimulated with PHA in the absence of DHA. The levels of expression of cytokines in lymphocytes from cats with IBD treated with PHA and DHA are similar to the levels of expression of cytokines in lymphocytes from healthy cats treated with PHA in the absence of DHA, suggesting that DHA normalizes the response of the lymphocytes from the cats with IBD to mitogen stimulation.

EPA also decreases the level of expression of IL-2 and IFN-γ in cats with IBD to a level similar to the level of expression of IL-2 and IFN-γ in the healthy cats stimulated with PHA in the absence of EPA. The levels of expression of cytokines in lymphocytes from cats with IBD treated with PHA and EPA are similar to the levels of expression of cytokines in lymphocytes from healthy cats treated with PHA in the absence of EPA, suggesting that EPA, like DHA, also normalizes the response of the lymphocytes from the cats with IBD to mitogen stimulation (although, as shown in Example 1, EPA does not decrease the level of lymphocyte proliferation in vitro).

In the specification, there have been disclosed typical preferred embodiments of the invention and, although specific terms are employed, they are used in a generic and descriptive sense only and not for purposes of limitation, the scope of the invention being set forth in the claims. Obviously many modifications and variations of the invention are possible in light of the above teachings. It is therefore to be understood that within the scope of the appended claims the invention may be practiced otherwise than as specifically described.

What is claimed is:

1. A method of preparing a composition suitable for treating inflammatory bowel disease in a feline in need thereof comprising incorporating into a companion animal food a therapeutically effective amount of eicosapentaenoic acid and docosahexaenoic acid, wherein the amount of docosahexaenoic acid in the composition is in an amount sufficient to provide the feline with a daily dosage of 6 to 165 mg/kg body weight of docosahexaenoic acid per day, wherein the ratio of eicosapentaenoic acid to docosahexaenoic acid in the composition is from about 1:1 to about 2:1.

2. The method of claim 1 wherein the composition further comprises at least one fatty acid selected from the group consisting of arachidonic acid, linoleic acid, and alpha-linoleic acid.

3. A composition prepared according to the method of claim 2, wherein the composition, when fed to a feline afflicted with inflammatory bowel disease as a sole diet provides a decrease in lymphocyte proliferation.

4. A method of preparing a composition suitable for treating inflammatory bowel disease in a feline in need thereof comprising incorporating into a medicament a therapeutically effective amount of eicosapentaenoic acid and docosahexaenoic acid, which when administered to the feline will provide a decrease in lymphocyte proliferation, wherein the ratio of eicosapentaenoic acid to docosahexaenoic acid in the composition is from about 1:1 to about 2:1.

5. The method of claim 4 wherein the medicament further comprises at least one fatty acid selected from the group consisting of arachidonic acid, linoleic acid, and alpha-linoleic acid.

* * * * *